United States Patent
Gronwald et al.

(10) Patent No.: US 10,906,012 B2
(45) Date of Patent: Feb. 2, 2021

(54) PROCESS FOR MAKING MEMBRANES

(71) Applicant: BASF SE, Ludwigshafen am Rhein (DE)

(72) Inventors: Oliver Gronwald, Heusenstamm (DE); Martin Weber, Maikammer (DE); Frank Rittig, Osthofen (DE); Martin Heijnen, Landsberg am Lech (DE); Henning Urch, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 209 days.

(21) Appl. No.: 15/758,641

(22) PCT Filed: Sep. 7, 2016

(86) PCT No.: PCT/EP2016/071064
§ 371 (c)(1),
(2) Date: Mar. 8, 2018

(87) PCT Pub. No.: WO2017/045985
PCT Pub. Date: Mar. 23, 2017

(65) Prior Publication Data
US 2018/0257044 A1  Sep. 13, 2018

(30) Foreign Application Priority Data

Sep. 17, 2015 (EP) .................. 15185604

(51) Int. Cl.
| | | |
|---|---|---|
| B01D 67/00 | (2006.01) | |
| B01D 71/34 | (2006.01) | |
| B01D 71/68 | (2006.01) | |
| C07C 235/06 | (2006.01) | |
| B01D 69/02 | (2006.01) | |
| B01D 61/00 | (2006.01) | |
| B01D 61/02 | (2006.01) | |

(52) U.S. Cl.
CPC .......... *B01D 71/68* (2013.01); *B01D 67/0011* (2013.01); *B01D 69/02* (2013.01); *B01D 71/34* (2013.01); *C07C 235/06* (2013.01); *B01D 61/002* (2013.01); *B01D 61/025* (2013.01); *B01D 67/0009* (2013.01); *B01D 2325/20* (2013.01)

(58) Field of Classification Search
None
See application file for complete search history.

(56) References Cited

U.S. PATENT DOCUMENTS

| | | | |
|---|---|---|---|
| 4,870,153 A | 9/1989 | Matzner et al. | |
| 2010/0133188 A1 | 6/2010 | Liu et al. | |
| 2014/0343178 A1* | 11/2014 | Mizokoshi | B01D 67/0011 521/77 |

FOREIGN PATENT DOCUMENTS

| | | | |
|---|---|---|---|
| CN | 101851865 A | 10/2010 | |
| CN | 102803362 A | 11/2012 | |
| CN | 104524994 A | 4/2015 | |
| EP | 0 113 112 A1 | 7/1984 | |
| EP | 0 135 130 A2 | 3/1985 | |
| EP | 0 297 363 A2 | 1/1989 | |
| WO | WO-2013039223 A1 * | 3/2013 | ............... C08J 9/26 |

OTHER PUBLICATIONS

Noel, Timothy—"Green is the future of chemistry: report of Taminco's second Green Footsteps Event at the i-SUP 2012"—Green Process Synth, 2012 (Year: 2012).*
Fendi Ye et al—CN 101851865 Machine Translation—Dec. 14, 2011 (Year: 2011).*
International Search Report dated Jan. 3, 2017 in PCT/EP2016/071064.
Boor Singh Lalia, et al., "A review on membrane fabrication: Structure, properties and performance relationship", Desalination, vol. 326, Aug. 2013, XP028705681, pp. 77-95.
Thierry Vidal, et al., "A New Environmentally Friendly Solvent of Low Toxicity for Crop Protection Formulations", Journal of ASTM International, vol. 8, No. 6, XP009171792, Jun. 2011, 8 pages.
Thierry Vidal, "Sustainable Solvents—Product and Process Innovations", XP055327876, Rhodia, Jun. 14, 2012, http://www.chemspeceurope.com/content-images/main/Conferences/Sustainable-Solvents-Products-and-Process-Innovations_Thierry-Vidal-RSC-Symposium-2012.pdf.
Office Action dated Jul. 3, 2020, in Chinese Patent Application No. 201680054389.5 (w/ Computer-generated English translation).

* cited by examiner

*Primary Examiner* — Bradley R Spies
(74) *Attorney, Agent, or Firm* — Oblon, McClelland, Maier & Neustadt, L.L.P.

(57) ABSTRACT

Process for making membranes M comprising the following steps: a) providing a dope solution D comprising at least one polymer P and at least one solvent S, b) adding at least one coagulant C to said dope solution D to coagulate said at least one polymer P from said dope solution D to obtain a membrane M, wherein said at least one solvent S comprises more than 50% by weight of at least one compound according to formula (I) (I), wherein $R^1$ and $R^2$ are independently $C_1$ to $C_{20}$ alkyl, $R^3$ is selected from H or an aliphatic rest, 20 $R^4$ is selected from H or an aliphatic rest, AO represents at least one alkylene oxide, n is a number from 0 to 100.

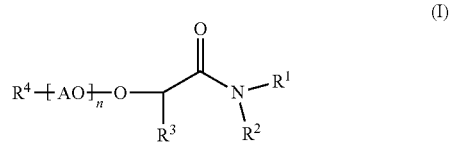

(I)

11 Claims, No Drawings

PROCESS FOR MAKING MEMBRANES

The present invention is related to processes for making membranes M comprising the following steps:
- a) providing a dope solution D comprising at least one polymer P and at least one solvent S,
- b) adding at least one coagulant C to said dope solution D to coagulate said at least one polymer P from said dope solution D to obtain a membrane M, wherein said at least one solvent S comprises more than 50% by weight of at least one compound according to formula (I)

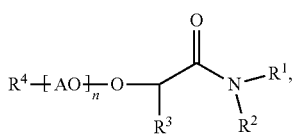

(I)

wherein $R^1$ and $R^2$ are independently $C_1$ to $C_{20}$ alkyl,
$R^3$ is selected from H or an aliphatic rest,
$R^4$ is selected from H or an aliphatic rest,
AO represents at least one alkylene oxide,
n is a number from 0 to 100.

It is further related to membranes obtained in such processes and to the use of such membranes.

Different types of membranes play an increasingly important role in many fields of technology. In particular, methods for treating water rely more and more on membrane technology.

There is a need for membranes with improved separation characteristics.

It was therefore an objective of the present invention to provide membranes with improved permeabilities and separation performance.

Said objective has been solved by processes according to claim 1.

In the context of this application a membrane shall be understood to be a thin, semi-permeable structure capable of separating two fluids or separating molecular and/or ionic components or particles from a liquid. A membrane acts as a selective barrier, allowing some particles, substances or chemicals to pass through, while retaining others.

For example, membranes M can be reverse osmosis (RO) membranes, forward osmosis (FO) membranes, nanofiltration (NF) membranes, ultrafiltration (UF) membranes or microfiltration (MF) membranes. These membrane types are generally known in the art and are further described below.

FO membranes are normally suitable for treatment of seawater, brackish water, sewage or sludge streams. Thereby pure water is removed from those streams through a FO membrane into a so called draw solution on the back side of the membrane having a high osmotic pressure.

In a preferred embodiment, suitable FO membranes are thin film composite (TFC) FO membranes. Preparation methods and use of thin film composite membranes are principally known and, for example described by R. J. Petersen in Journal of Membrane Science 83 (1993) 81-150.

In a particularly preferred embodiment, suitable FO membranes comprise a fabric layer, a support layer, a separation layer and optionally a protective layer. Said protective layer can be considered an additional coating to smoothen and/or hydrophilize the surface.

Said fabric layer can for example have a thickness of 10 to 500 μm. Said fabric layer can for example be a woven or nonwoven, for example a polyester nonwoven.

Said support layer of a TFC FO membrane normally comprises pores with an average pore diameter of for example 0.5 to 100 nm, preferably 1 to 40 nm, more preferably 5 to 20 nm. Said support layer can for example have a thickness of 5 to 1000 μm, preferably 10 to 200 μm. Said support layer may for example comprise as the main component a polysulfone, polyethersulfone, polyphenylenesulfone, polyvinylidenedifluoride, polyimide, polyimideurethane or cellulose acetate. Processes according to the invention are especially suitable for making the support layer of FO membranes.

In one embodiment, FO membranes comprise a support layer comprising as the main component at least one polyamide (PA), polyvinylalcohol (PVA), Cellulose Acetate (CA), Cellulose Triacetate (CTA), CA-triacetate blend, Cellulose ester, Cellulose Nitrate, regenerated Cellulose, aromatic, aromatic/aliphatic or aliphatic Polyamide, aromatic, aromatic/aliphatic or aliphatic Polyimide, Polybenzimidazole (PBI), Polybenzimidazolone (PBIL), Polyacrylonitrile (PAN), PAN-poly(vinyl chloride) copolymer (PAN-PVC), PAN-methallyl sulfonate copolymer, polyetherimide (PEI), Polyetheretherketone (PEEK), sulfonated polyetheretherketone (SPEEK), Poly(dimethylphenylene oxide) (PPO), Polycarbonate, Polyester, Polytetrafluroethylene (PTFE), Poly (vinylidene fluoride) (PVDF), Polypropylene (PP), Polyelectrolyte complexes, Poly(methyl methacrylate) PMMA, Polydimethylsiloxane (PDMS), aromatic, aromatic/aliphatic or aliphatic polyimide urethanes, aromatic, aromatic/aliphatic or aliphatic polyamidimides, crosslinked polyimides or polyarylene ether, polysulfone (PSU), polyphenylenesulfone (PPSU) or polyethersulfone (PESU), or mixtures thereof.

Said separation layer of a FO membrane can for example have a thickness of 0.05 to 1 μm, preferably 0.1 to 0.5 μm, more preferably 0.15 to 0.3 μm. Preferably, said separation layer can for example comprise polyamide or cellulose acetate as the main component.

Optionally, TFC FO membranes can comprise a protective layer with a thickness of 30-500 preferable 100-300 nm. Said protective layer can for example comprise polyvinylalcohol (PVA) as the main component. In one embodiment, the protective layer comprises a halamine like chloramine.

In one preferred embodiment, suitable membranes are TFC FO membranes comprising a support layer comprising at least one polysulfone, polyphenylenesulfone and/or polyethersulfone obtained by processes according to the invention, a separation layer comprising polyamide as main component and optionally a protective layer comprising polyvinylalcohol as the main component.

In a preferred embodiment suitable FO membranes comprise a separation layer obtained from the condensation of a polyamine and a polyfunctional acyl halide. Said separation layer can for example be obtained in an interfacial polymerization process.

RO membranes are normally suitable for removing molecules and ions, in particular monovalent ions. Typically, RO membranes are separating mixtures based on a solution/diffusion mechanism.

In a preferred embodiment, suitable membranes are thin film composite (TFC) RO membranes. Preparation methods and use of thin film composite membranes are principally known and, for example described by R. J. Petersen in Journal of Membrane Science 83 (1993) 81-150.

In a further preferred embodiment, suitable RO membranes comprise a fabric layer, a support layer, a separation layer and optionally a protective layer. Said protective layer can be considered an additional coating to smoothen and/or hydrophilize the surface Said fabric layer can for example have a thickness of 10 to 500 µm. Said fabric layer can for example be a woven or nonwoven, for example a polyester nonwoven.

Said support layer of a TFC RO membrane normally comprises pores with an average pore diameter of for example 0.5 to 100 nm, preferably 1 to 40 nm, more preferably 5 to 20 nm. Said support layer can for example have a thickness of 5 to 1000 µm, preferably 10 to 200 µm. Said support layer may for example comprise as the main component a polysulfone, polyethersulfone, polyphenylenesulfone, PVDF, polyimide, polyimideurethane or cellulose acetate.

In one embodiment, RO membranes comprise a support layer comprising as the main component at least one polyamide (PA), polyvinylalcohol (PVA), Cellulose Acetate (CA), Cellulose Triacetate (CTA), CA-triacetate blend, Cellulose ester, Cellulose Nitrate, regenerated Cellulose, aromatic, aromatic/aliphatic or aliphatic Polyamide, aromatic, aromatic/aliphatic or aliphatic Polyimide, Polybenzimidazole (PBI), Polybenzimidazolone (PBIL), Polyacrylonitrile (PAN), PAN-poly(vinyl chloride) copolymer (PAN-PVC), PAN-methallyl sulfonate copolymer, polyetherimide (PEI), Polyetheretherketone (PEEK), sulfonated polyetheretherketone (SPEEK), Poly(dimethylphenylene oxide) (PPO), Polycarbonate, Polyester, Polytetrafluroethylene (PTFE), Poly(vinylidene fluoride) (PVDF), Polypropylene (PP), Polyelectrolyte complexes, Poly(methyl methacrylate) PMMA, Polydimethylsiloxane (PDMS), aromatic, aromatic/aliphatic or aliphatic polyimide urethanes, aromatic, aromatic/aliphatic or aliphatic polyamidimides, crosslinked polyimides or polyarylene ether, polysulfone, polyphenylenesulfone or polyethersulfone, or mixtures thereof.

In another preferred embodiment, RO membranes comprise a support layer comprising as the main component at least one polysulfone, polyphenylenesulfone and/or polyethersulfone. Processes according to the invention are especially suitable for making the support layer of RO membranes.

Said separation layer can for example have a thickness of 0.02 to 1 µm, preferably 0.03 to 0.5 µm, more preferably 0.05 to 0.3 µm. Preferably said separation layer can for example comprise polyamide or cellulose acetate as the main component.

Optionally, TFC RO membranes can comprise a protective layer with a thickness of 5 to 500 preferable 10 to 300 nm. Said protective layer can for example comprise polyvinylalcohol (PVA) as the main component. In one embodiment, the protective layer comprises a halamine like chloramine.

In one preferred embodiment, suitable membranes are TFC RO membranes comprising a nonwoven polyester fabric, a support layer comprising at least one polysulfone, polyphenylenesulfone and/or polyethersulfone obtained by processes according to the invention, a separation layer comprising polyamide as main component and optionally a protective layer comprising polyvinylalcohol as the main component.

In a preferred embodiment suitable RO membranes comprise a separation layer obtained from the condensation of a polyamine and a polyfunctional acyl halide. Said separation layer can for example be obtained in an interfacial polymerization process.

Suitable polyamine monomers can have primary or secondary amino groups and can be aromatic (e. g. a diaminobenzene, a triaminobenzene, m-phenylenediamine, p-phenylenediamine, 1,3,5-triaminobenzene, 1,3,4-triaminobenzene, 3,5-diaminobenzoic acid, 2,4-diaminotoluene, 2,4-diaminoanisole, and xylylenediamine) or aliphatic (e. g. ethylenediamine, propylenediamine, piperazine, and tris(2-diaminoethyl)amine).

Suitable polyfunctional acyl halides include trimesoyl chloride (TMC), trimellitic acid chloride, isophthaloyl chloride, terephthaloyl chloride and similar compounds or blends of suitable acyl halides. As a further example, the second monomer can be a phthaloyl halide.

In one embodiment of the invention, a separation layer of polyamide is made from the reaction of an aqueous solution of meta-phenylene diamine MPD with a solution of trimesoyl chloride (TMC) in an apolar solvent.

NF membranes are normally especially suitable for removing multivalent ions and large monovalent ions. Typically, NF membranes function through a solution/diffusion or/and filtration-based mechanism.

NF membranes are normally used in crossflow filtration processes.

In one embodiment, NF membranes comprise as the main component at least one polyamide (PA), polyvinylalcohol (PVA), Cellulose Acetate (CA), Cellulose Triacetate (CTA), CA-triacetate blend, Cellulose ester, Cellulose Nitrate, regenerated Cellulose, aromatic, aromatic/aliphatic or aliphatic Polyamide, aromatic, aromatic/aliphatic or aliphatic Polyimide, Polybenzimidazole (PBI), Polybenzimidazolone (PBIL), Polyacrylonitrile (PAN), PAN-poly(vinyl chloride) copolymer (PAN-PVC), PAN-methallyl sulfonate copolymer, polyetherimide (PEI), Polyetheretherketone (PEEK), sulfonated polyetheretherketone (SPEEK), Poly(dimethylphenylene oxide) (PPO), Polycarbonate, Polyester, Polytetrafluroethylene (PTFE), Poly(vinylidene fluoride) (PVDF), Polypropylene (PP), Polyelectrolyte complexes, Poly(methyl methacrylate) PMMA, Polydimethylsiloxane (PDMS), aromatic, aromatic/aliphatic or aliphatic polyimide urethanes, aromatic, aromatic/aliphatic or aliphatic polyamidimides, crosslinked polyimides or polyarylene ether, polysulfone, polyphenylenesulfone or polyethersulfone, or mixtures thereof.

In another embodiment of the invention, NF membranes comprise as the main component at least one polysulfone, polyphenylenesulfone and/or polyethersulfone.

In a particularly preferred embodiment, the main components of a NF membrane are positively or negatively charged.

Nanofiltration membranes often comprise charged polymers comprising sulfonic acid groups, carboxylic acid groups and/or ammonium groups in combination with block copolymers according to the invention.

In another embodiment, NF membranes comprise as the main component polyamides, poly-imides or polyimide urethanes, Polyetheretherketone (PEEK) or sulfonated polyetheretherketone (SPEEK).

UF membranes are normally suitable for removing suspended solid particles and solutes of high molecular weight, for example above 10000 Da. In particular, UF membranes are normally suitable for removing bacteria and viruses.

UF membranes normally have an average pore diameter of 2 nm to 50 nm, preferably 5 to 40 nm, more preferably 5 to 20 nm.

In one embodiment, UF membranes comprise as the main component at least one polyamide (PA), polyvinylalcohol (PVA), Cellulose Acetate (CA), Cellulose Triacetate (CTA), CA-triacetate blend, Cellulose ester, Cellulose Nitrate, regenerated Cellulose, aromatic, aromatic/aliphatic or aliphatic Polyamide, aromatic, aromatic/aliphatic or aliphatic Polyimide, Polybenzimidazole (PBI), Polybenzimidazolone (PBIL), Polyacrylonitrile (PAN), PAN-poly(vinyl chloride) copolymer (PAN-PVC), PAN-methallyl sulfonate copolymer, polyetherimide (PEI), Polyetheretherketone (PEEK), sulfonated polyetheretherketone (SPEEK), Poly(dimethylphenylene oxide) (PPO), Polycarbonate, Polyester, Polytetrafluroethylene PTFE, Poly(vinylidene fluoride) (PVDF), Polypropylene (PP), Polyelectrolyte complexes, Poly(methyl methacrylate) PMMA, Polydimethylsiloxane (PDMS), aromatic, aromatic/aliphatic or aliphatic polyimide urethanes, aromatic, aromatic/aliphatic or aliphatic polyamidimides, crosslinked polyimides or polyarylene ether, polysulfone, polyphenylenesulfone, or polyethersulfone, or mixtures thereof.

In another embodiment of the invention, UF membranes comprise as the main component at least one polysulfone, polyphenylenesulfone and/or polyethersulfone.

"Polysulfones", "polyethersulfones" and "polyphenylenesulfones" shall include the respective polymers that comprise sulfonic acid and/or salts of sulfonic acid at some of the aromatic moieties.

In one embodiment, UF membranes comprise as the main component or as an additive at least one partly sulfonated polysulfone, partly sulfonated polyphenylenesulfone and/or partly sulfonated polyethersulfone. In one embodiment, UF membranes comprise as the main component or as an additive at least one partly sulfonated polyphenylenesulfone.

"Arylene ethers", "Polysulfones", "polyethersulfones" and "polyphenylenesulfones" shall include block polymers that comprise blocks of the respective arylene ethers, Polysulfones, polyethersulfones or polyphenylenesulfones as well as other polymer blocks.

In one embodiment, UF membranes comprise as the main component or as an additive at least one block copolymer of at least one arylene ether and at least one polyalkylene oxide. In one embodiment, UF membranes comprise as the main component or as an additive at least one block copolymer of at least one polysulfone or polyethersulfone and at least one polyalkylene oxide like polyethylene oxide, In one embodiment, UF membranes comprise further additives like polyvinyl pyrrolidones or polyalkylene oxides like polyethylene oxides.

In a preferred embodiment, UF membranes comprise as major components polysulfones, polyphenylenesulfone or polyethersulfone in combination with additives like polyvinylpyrrolidone.

In one preferred embodiment, UF membranes comprise 99.9 to 50% by weight of a combination of polyethersulfone and 0.1 to 50% by weight of polyvinylpyrrolidone.

In another preferred embodiment UF membranes comprise 95 to 80% by weight of polyethersulfone and 5 to 15% by weight of polyvinylpyrrolidone.

In one embodiment of the invention, UF membranes are present as spiral wound membranes, as pillows or flat sheet membranes.

In another embodiment of the invention, UF membranes are present as tubular membranes.

In another embodiment of the invention, UF membranes are present as hollow fiber membranes or capillaries.

In yet another embodiment of the invention, UF membranes are present as single bore hollow fiber membranes.

In yet another embodiment of the invention, UF membranes are present as multibore hollow fiber membranes.

Multiple channel membranes, also referred to as multi-bore membranes, comprise more than one longitudinal channels also referred to simply as "channels".

In a preferred embodiment, the number of channels is typically 2 to 19. In one embodiment, multiple channel membranes comprise two or three channels. In another embodiment, multiple channel membranes comprise 5 to 9 channels. In one preferred embodiment, multiple channel membranes comprise seven channels.

In another embodiment the number of channels is 20 to 100.

The shape of such channels, also referred to as "bores", may vary. In one embodiment, such channels have an essentially circular diameter. In another embodiment, such channels have an essentially ellipsoid diameter. In yet another embodiment, channels have an essentially rectangular diameter.

In some cases, the actual form of such channels may deviate from the idealized circular, ellipsoid or rectangular form.

Normally, such channels have a diameter (for essentially circular diameters), smaller diameter (for essentially ellipsoid diameters) or smaller feed size (for essentially rectangular diameters) of 0.05 mm to 3 mm, preferably 0.5 to 2 mm, more preferably 0.9 to 1.5 mm. In another preferred embodiment, such channels have a diameter (for essentially circular diameters), smaller diameter (for essentially ellipsoid diameters) or smaller feed size (for essentially rectangular diameters) in the range from 0.2 to 0.9 mm.

For channels with an essentially rectangular shape, these channels can be arranged in a row.

For channels with an essentially circular shape, these channels are in a preferred embodiment arranged such that a central channel is surrounded by the other channels. In one preferred embodiment, a membrane comprises one central channel and for example four, six or 18 further channels arranged cyclically around the central channel.

The wall thickness in such multiple channel membranes is normally from 0.02 to 1 mm at the thinnest position, preferably 30 to 500 µm, more preferably 100 to 300 µm.

Normally, the membranes according to the invention and carrier membranes have an essentially circular, ellipsoid or rectangular diameter. Preferably, membranes according to the invention are essentially circular.

In one preferred embodiment, membranes according to the invention have a diameter (for essentially circular diameters), smaller diameter (for essentially ellipsoid diameters) or smaller feed size (for essentially rectangular diameters) of 2 to 10 mm, preferably 3 to 8 mm, more preferably 4 to 6 mm.

In another preferred embodiment, membranes according to the invention have a diameter (for essentially circular diameters), smaller diameter (for essentially ellipsoid diameters) or smaller feed size (for essentially rectangular diameters) of 2 to 4 mm.

In one embodiment the rejection layer is located on the inside of each channel of said multiple channel membrane.

In one embodiment, the channels of a multibore membrane may incorporate an active layer with a pore size different to that of the carrier membrane or a coated layer forming the active layer. Suitable materials for the coated layer are polyoxazoline, polyethylene glycol, polystyrene, hydrogels, polyamide, zwitterionic block copolymers, such as sulfobetaine or carboxybetaine. The active layer can have a thickness in the range from 10 to 500 nm, preferably from 50 to 300 nm, more preferably from 70 to 200 nm.

In one embodiment multibore membranes are designed with pore sizes between 0.2 and 0.01 µm. In such embodiments the inner diameter of the capillaries can lie between 0.1 and 8 mm, preferably between 0.5 and 4 mm and particularly preferably between 0.9 and 1.5 mm. The outer diameter of the multibore membrane can for example lie between 1 and 26 mm, preferred 2.3 and 14 mm and particularly preferred between 3.6 and 6 mm. Furthermore, the multibore membrane can contain 2 to 94, preferably 3 to 19 and particularly preferred between 3 and 14 channels. Often multibore membranes contain seven channels. The permeability range can for example lie between 100 and 10000 L/m²hbar, preferably between 300 and 2000 L/m²hbar.

Typically multibore membranes of the type described above are manufactured by extruding a polymer, which forms a semi-permeable membrane after coagulation through an extrusion nozzle with several hollow needles. A coagulating liquid is injected through the hollow needles into the extruded polymer during extrusion, so that parallel continuous channels extending in extrusion direction are formed in the extruded polymer. Preferably the pore size on an outer surface of the extruded membrane is controlled by bringing the outer surface after leaving the extrusion nozzle in contact with a mild coagulation agent such that the shape is fixed without active layer on the outer surface and subsequently the membrane is brought into contact with a strong coagulation agent. As a result a membrane can be obtained that has an active layer inside the channels and an outer surface, which exhibits no or hardly any resistance against liquid flow. Herein suitable coagulation agents include solvents and/or non-solvents. The strength of the coagulations may be adjusted by the combination and ratio of nonsolvent/solvent. Coagulation solvents are known to the person skilled in the art and can be adjusted by routine experiments. An example for a solvent based coagulation agent is N-methylpyrrolidone. Non-solvent based coagulation agents are for instance water, iso-propanol and propylene glycol.

MF membranes are normally suitable for removing particles with a particle size of 0.1 µm and above.

MF membranes normally have an average pore diameter of 0.05 µm to 10 µm, preferably 1.0 µm to 5 µm.

Microfiltration can use a pressurized system but it does not need to include pressure.

MF membranes can be capillaries, hollow fibers, flat sheet, tubular, spiral wound, pillows, hollow fine fiber or track etched. They are porous and allow water, monovalent species (Na+, Cl−), dissolved organic matter, small colloids and viruses through but retain particles, sediment, algae or large bacteria.

Microfiltration systems are designed to remove suspended solids down to 0.1 micrometers in size, in a feed solution with up to 2-3% in concentration.

In one embodiment, MF membranes comprise as the main component at least polyimide (PA), polyvinylalcohol (PVA), Cellulose Acetate (CA), Cellulose Triacetate (CTA), CA-triacetate blend, Cellulose ester, Cellulose Nitrate, regenerated Cellulose, aromatic, aromatic/aliphatic or aliphatic Polyamide, aromatic, aromatic/aliphatic or aliphatic Polyimide, Polybenzimidazole (PBI), Polybenzimidazolone (PBIL), Polyacrylonitrile (PAN), PAN-poly(vinyl chloride) copolymer (PAN-PVC), PAN-methallyl sulfonate copolymer, polyetherimide (PEI), Polyetheretherketone (PEEK), sulfonated polyetheretherketone (SPEEK), Poly(dimethylphenylene oxide) (PPO), Polycarbonate, Polyester, Polytetrafluroethylene PTFE, Poly(vinylidene fluoride) (PVDF), Polypropylene (PP), Polyelectrolyte complexes, Poly(methyl methacrylate) PMMA, Polydimethylsiloxane (PDMS), aromatic, aromatic/aliphatic or aliphatic polyimide urethanes, aromatic, aromatic/aliphatic or aliphatic polyamidimides, crosslinked polyimides or polyarylene ether, polysulfone, polyphenylenesulfone or polyethersulfone, or mixtures thereof.

In another embodiment of the invention, MF membranes comprise as the main component at least one polysulfone, polyphenylenesulfone and/or polyethersulfone.

In one embodiment, MF membranes comprise as the main component at least one partly sulfonated polysulfone, partly sulfonated polyphenylenesulfone and/or partly sulfonated polyethersulfone. In one embodiment, MF membranes comprise as the main component at least one partly sulfonated polyphenylenesulfone.

In one embodiment, MF membranes comprise as the main component or as an additive at least one block copolymer of at least one arylene ether and at least one polyalkylene oxide. In one embodiment, MF membranes comprise as the main component or as an additive at least one block copolymer of at least one polysulfone or polyethersulfone and at least one polyalkylene oxide like polyethylene oxide.

Membranes M are prepared by providing in step a) a dope solution D comprising at least one polymer P and at least one solvent S.

Suitable polymers P are in principle all polymers that are suitable for making membranes or parts of membranes like carrier membranes for RO or FO membranes.

Preferably, polymer P is selected from polyamide (PA), polyvinylalcohol (PVA), Cellulose Acetate (CA), Cellulose Triacetate (CTA), CA-triacetate blend, Cellulose ester, Cellulose Nitrate, regenerated Cellulose, aromatic, aromatic/aliphatic or aliphatic Polyamide, aromatic, aromatic/aliphatic or aliphatic Polyimide, Polybenzimidazole (PBI), Polybenzimidazolone (PBIL), Polyacrylonitrile (PAN), PAN-poly(vinyl chloride) copolymer (PAN-PVC), PAN-methallyl sulfonate copolymer, polyetherimide (PEI), Polyetheretherketone (PEEK), sulfonated polyetheretherketone (SPEEK), Poly(dimethylphenylene oxide) (PPO), Polycarbonate, Polyester, Polytetrafluroethylene (PTFE), Poly(vinylidene fluoride) (PVDF), Polypropylene (PP), Polyelectrolyte complexes, Poly(methyl methacrylate) PMMA, Polydimethylsiloxane (PDMS), aromatic, aromatic/aliphatic or aliphatic polyimide urethanes, aromatic, aromatic/aliphatic or aliphatic polyamidimides, crosslinked polyimides or polyarylene ether, polysulfone (PSU), polyphenylenesulfone (PPSU) or polyethersulfone (PESU), or mixtures thereof.

More preferably, polymer P is selected from Poly(vinylidene fluoride) (PVDF) or polyarylene ethers like polysulfone (PSU), polyphenylenesulfone (PPSU) or polyethersulfone (PESU), or mixtures thereof.

In one embodiment, membranes M comprise as the main component or as an additive at least one polymer P that is a partly sulfonated polysulfone, partly sulfonated polyphenylenesulfone and/or partly sulfonated polyethersulfone. In one embodiment, membranes M comprise as the main component at least one partly sulfonated polyphenylenesulfone.

In one embodiment, membranes M comprise as the main component or as an additive at least one polymer P that is a block copolymer of at least one arylene ether and at least one polyalkylene oxide. In one embodiment, membranes M comprise as the main component or as an additive at least one block copolymer of at least one polysulfone or polyethersulfone and at least one polyalkylene oxide like polyethylene oxide.

In one embodiment, polymer P is a polyarylene ether.

Suitable polyarylene ethers are known as such to those skilled in the art and can be formed from polyarylene ether units of the general formula IV Preferably, Q, T and Y in formula (IV), however, are independently selected from —O— and —SO$_2$—, with the proviso that at least one of the group consisting of Q, T and Y is —SO$_2$—.

When Q, T or Y are —CR$^a$R$^b$—, R$^a$ and R$^b$ are each independently a hydrogen atom or a C$_1$-C$_{12}$-alkyl, C$_1$-C$_{12}$-alkoxy or C$_6$-C$_{18}$-aryl group.

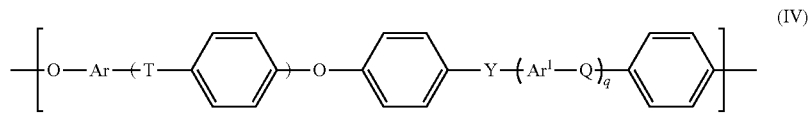

(IV)

with the following definitions:

t, q: each independently 0, 1, 2 or 3,

Q, T, Y: each independently a chemical bond or group selected from —O—, —S—, —SO$_2$—, S=O, C=O, —N=N—, —CR$^a$R$^b$— where R$^a$ and R$^b$ are each independently a hydrogen atom or a C$_1$-C$_{12}$-alkyl, C$_1$-C$_{12}$-alkoxy or C$_6$-C$_{18}$-aryl group, where at least one of Q, T and Y is not —O—, and at least one of Q, T and Y is —SO$_2$—, and Ar, Ar$^1$: each independently an arylene group having from 6 to 18 carbon atoms Polyarylene ethers are typically prepared by polycondensation of suitable starting compounds in dipolar aprotic solvents at elevated temperature (see, for example, R. N. Johnson et al., J. Polym. Sci. A-1 5 (1967) 2375, J. E. McGrath et al., Polymer 25 (1984) 1827).

Suitable polyarylene ethers can be provided by reacting at least one starting compound of the structure X—Ar—Y (M1) with at least one starting compound of the structure HO—Ar$^1$—OH (M2) in the presence of a solvent (L) and of a base (B), where Y is a halogen atom, X is selected from halogen atoms and OH, preferably from halogen atoms, especially F, Cl or Br, and Ar and Ar$^1$ are each independently an arylene group having 6 to 18 carbon atoms.

In one embodiment, a polyarylene ether which is formed from units of the general formula IV with the definitions as above is provided in the presence of a solvent (L):

Preferred C$_1$-C$_{12}$-alkyl groups comprise linear and branched, saturated alkyl groups having from 1 to 12 carbon atoms. Particularly preferred C$_1$-C$_{12}$-alkyl groups are: C$_1$-C$_6$-alkyl radicals such as methyl, ethyl, n-propyl, isopropyl, n-butyl, sec-butyl, 2- or 3-methylpentyl and longer-chain radicals such as unbranched heptyl, octyl, nonyl, decyl, undecyl, lauryl, and the singularly or multiply branched analogs thereof.

Useful alkyl radicals in the aforementioned usable C$_1$-C$_{12}$-alkoxy groups include the alkyl groups having from 1 to 12 carbon atoms defined above. Cycloalkyl radicals usable with preference comprise especially C$_3$-C$_{12}$-cycloalkyl radicals, for example cyclopropyl, cyclobutyl, cyclopentyl, cyclohexyl, cycloheptyl, cyclooctyl, cyclopropylmethyl, cyclopropylethyl, cyclopropylpropyl, cyclobutylmethyl, cyclobutylethyl, cyclpentylethyl, -propyl, -butyl, -pentyl, -hexyl, cyclohexylmethyl, -dimethyl, -trimethyl.

Ar and Ar$^1$ are each independently a C$_6$-C$_{18}$-arylene group. Proceeding from the starting materials described below, Ar is preferably derived from an electron-rich aromatic substance which is preferably selected from the group consisting of hydroquinone, resorcinol, dihydroxynaphthalene, especially 2,7-dihydroxynaphthalene, and 4,4'-bisphenol. Ar$^1$ is preferably an unsubstituted C$_6$- or C$_{12}$-arylene group.

Useful C$_6$-C$_{18}$-arylene groups Ar and Ar$^1$ are especially phenylene groups, such as 1,2-, 1,3- and 1,4-phenylene, naphthylene groups, for example 1,6-, 1,7-, 2,6- and 2,7-

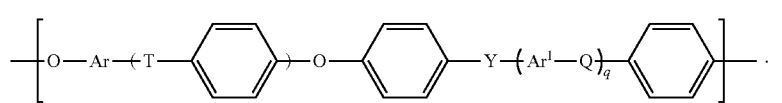

(IV)

If Q, T or Y, with the abovementioned prerequisites, is a chemical bond, this is understood to mean that the group adjacent to the left and the group adjacent to the right are bonded directly to one another via a chemical bond.

naphthylene, and the arylene groups derived from anthracene, phenanthrene and naphthacene.

Preferably, Ar and Ar$^1$ in the preferred embodiments of the formula (IV) are each independently selected from the group consisting of 1,4-phenylene, 1,3-phenylene, naphthylene, especially 2,7-dihydroxynaphthalene, and 4,4'-bisphenylene.
Units present with preference within the polyarylene ether are those which comprise at least one of the following repeat structural units IVa to IVo:
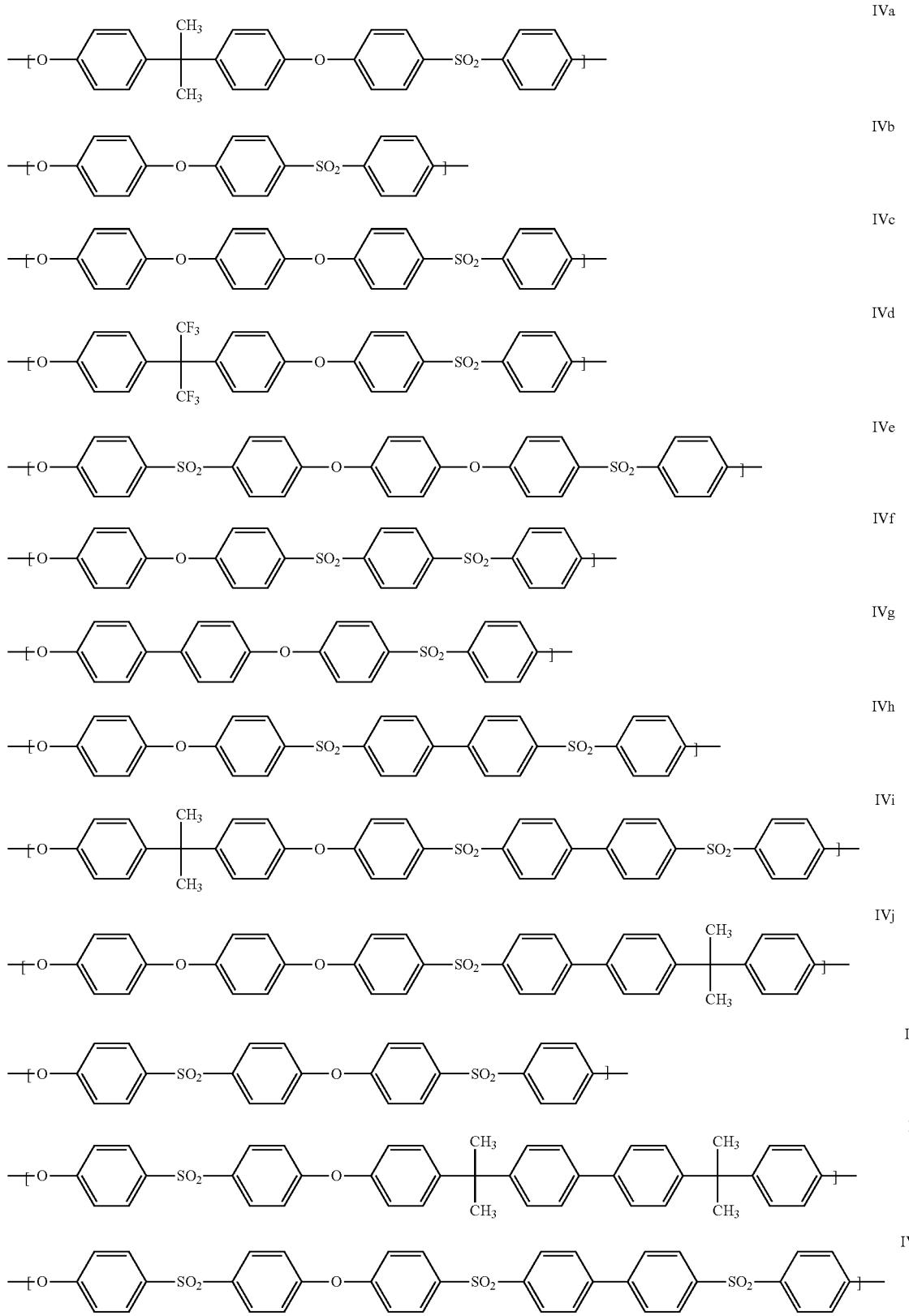

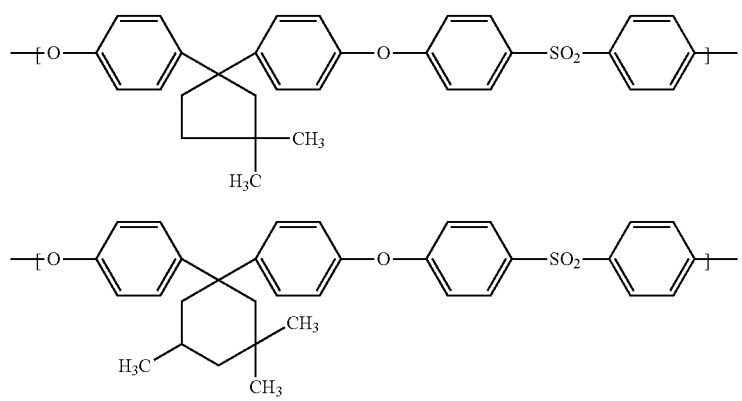

In addition to the units IVa to IVo present with preference, preference is also given to those units in which one or more 1,4-dihydroxyphenyl units are replaced by resorcinol or dihydroxynaphthalene units.

Particularly preferred units of the general formula II are units IVa, IVg and IVk. It is also particularly preferred when the polyarylene ethers A are formed essentially from one kind of units of the general formula IV, especially from one unit selected from IVa, IVg and IVk.

In a particularly preferred embodiment, Ar=1,4-phenylene, t=1, q=0, T=SO$_2$ and Y=SO$_2$. Such polyarylene ethers are referred to as polyether sulfone (PSU).

Suitable polyarylene ethers A preferably have a mean molecular weight Mn (number average) in the range from 2000 to 70000 g/mol, especially preferably 5000 to 40000 g/mol and particularly preferably 7000 to 30000 g/mol. The average molecular weight of the polyarylene ethers can be controlled and calculated by the ratio of the monomers forming the polyarylene ethers, as described by H. G. Elias in "An Introduction to Polymer Science" VCH Weinheim, 1997, p. 125.

Suitable starting compounds are known to those skilled in the art and are not subject to any fundamental restriction, provided that the substituents mentioned are sufficiently reactive within a nucleophilic aromatic substitution.

Preferred starting compounds are difunctional. "Difunctional" means that the number of groups reactive in the nucleophilic aromatic substitution is two per starting compound. A further criterion for a suitable difunctional starting compound is a sufficient solubility in the solvent, as explained in detail below.

Preference is given to monomeric starting compounds, which means that the reaction is preferably performed proceeding from monomers and not proceeding from prepolymers.

The starting compound (M1) used is preferably a dihalodiphenyl sulfone. The starting compound (M2) used is preferably dihydroxydiphenyl sulfone.

Suitable starting compounds (M1) are especially dihalodiphenyl sulfones such as 4,4'-dichlorodiphenyl sulfone, 4,4'-difluorodiphenyl sulfone, 4,4'-dibromodiphenyl sulfone, bis(2-chlorophenyl) sulfones, 2,2'-dichlorodiphenyl sulfone and 2,2'-difluorodiphenyl sulfone, particular preference being given to 4,4'-dichlorodiphenyl sulfone and 4,4'-difluorodiphenyl sulfone.

Preferred compounds (M2) are accordingly those having two phenolic hydroxyl groups.

Phenolic OH groups are preferably reacted in the presence of a base in order to increase the reactivity towards the halogen substituents of the starting compound (M1).

Preferred starting compounds (M2) having two phenolic hydroxyl groups are selected from the following compounds:
dihydroxybenzenes, especially hydroquinone and resorcinol;
dihydroxynaphthalenes, especially 1,5-dihydroxynaphthalene,
1,6-dihydroxynaphthalene, 1,7-dihydroxynaphthalene, and 2,7-dihydroxynaphthalene; dihydroxybiphenyls, especially 4,4'-biphenol
and 2,2'-biphenol; bisphenyl ethers, especially bis(4-hydroxyphenyl) ether
and bis(2-hydroxyphenyl) ether; bisphenylpropanes, especially
2,2-bis(4-hydroxyphenyl)propane, 2,2-bis(3-methyl-4-hydroxyphenyl)propane
and 2,2-bis(3,5-dimethyl-4-hydroxyphenyl)propane;
bisphenylmethanes, especially bis(4-hydroxyphenyl)methane;
bisphenyl sulfones, especially bis(4-hydroxyphenyl) sulfone;
bisphenyl sulfides, especially bis(4-hydroxyphenyl) sulfide;
bisphenyl ketones, especially bis(4-hydroxyphenyl) ketone;
bisphenylhexafluoropropanes, especially 2,2-bis(3,5-dimethyl-4-hydroxyphenyl)hexafluoropropane; and
bisphenylfluorenes, especially 9,9-bis(4-hydroxyphenyl) fluorene;
1,1-Bis(4-hydroxyphenyl)-3,3,5-trimethyl-cyclohexane (bisphenol TMC).

It is preferable, proceeding from the aforementioned aromatic dihydroxyl compounds (M2), by addition of a base (B), to prepare the dipotassium or disodium salts thereof and to react them with the starting compound (M1). The aforementioned compounds can additionally be used individually or as a combination of two or more of the aforementioned compounds.

Hydroquinone, resorcinol, dihydroxynaphthalene, especially 2,7-dihydroxynaphthalene, bisphenol A, dihydroxydiphenyl sulfone and 4,4'-bisphenol are particularly preferred as starting compound (M2).

However, it is also possible to use trifunctional compounds. In this case, branched structures are the result. If a trifunctional starting compound (M2) is used, preference is given to 1,1,1-tris(4-hydroxyphenyl)ethane.

The ratios to be used derive in principle from the stoichiometry of the polycondensation reaction which proceeds with theoretical elimination of hydrogen chloride, and are established by the person skilled in the art in a known manner.

Preferably, the conversion in the polycondensation is at least 0.9, which ensures a sufficiently high molecular weight.

Solvents (L) preferred in the context of the present invention are organic, especially aprotic polar solvents. Suitable solvents also have a boiling point in the range from 80 to 320° C., especially 100 to 280° C., preferably from 150 to 250° C. Suitable aprotic polar solvents are, for example, high-boiling ethers, esters, ketones, asymmetrically halogenated hydrocarbons, anisole, dimethylformamide, dimethyl sulfoxide, sulfolane, N-methyl-2-pyrrolidone and/or N-ethyl-2-pyrrolidone. It is also possible to use mixtures of these solvents.

A preferred solvent is especially N-methyl-2-pyrrolidone and/or N-ethyl-2-pyrrolidone.

Preferably, the starting compounds (M1) and (M2) are reacted in the aprotic polar solvents (L) mentioned, especially N-methyl-2-pyrrolidone.

In a preferred embodiment the starting compounds (M1) and (M2) are reacted in the presence of a base (B). The bases are preferably anhydrous. Suitable bases are especially anhydrous alkali metal and/or alkaline earth metal carbonate, preferably sodium carbonate, potassium carbonate, calcium carbonate or mixtures thereof, very particular preference being given to potassium carbonate, especially potassium carbonate with a volume-weighted mean particle size of less than 200 micrometers, determined with a particle size measuring instrument in a suspension of N-methyl-2-pyrrolidone.

A particularly preferred combination is N-methyl-2-pyrrolidone as solvent (L) and potassium carbonate as base (B).

The reaction of the suitable starting compounds (M1) and (M2) is performed at a temperature of 80 to 250° C., preferably 100 to 220° C., the upper temperature limit being determined by the boiling point of the solvent.

The reaction is effected preferably within a time interval of 2 to 12 h, especially of 3 to 8 h.

Especially suitable starting materials, bases, solvents, ratios of all components involved, reaction times and reaction parameters like temperatures and pressures as well as suitable workup procedures are for example disclosed in U.S. Pat. No. 4,870,153, col. 4, ln. 11 to col. 17, ln. 64, EP 113 112, p. 6, ln. 1 to p. 9, ln. 14, EP-A 297 363, p. 10, ln. 38 to p. 11, ln. 24, EP-A 135 130, p. 1, ln. 37 to p. 4, ln. 20, which are incorporated in this application by reference.

In one especially preferred embodiment, polymer P is a polyethersulfone.

In one especially preferred embodiment, polymer P is a polysulfone.

In one especially preferred embodiment, polymer P is a polyphenylenesulfone.

In one embodiment, polymer P is a mixture of a polyethersulfone and a block copolymer comprising polyethersulfone blocks and polyalkyleneoxide blocks.

According to the invention, said at least one solvent S comprises more than 50% by weight, preferably more than 70% by weight, more preferably more than 90% by weight and especially preferably more than 95% by weight of at least one compound according to formula (I)

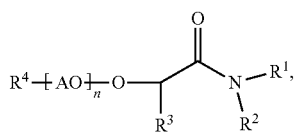

wherein $R^1$ and $R^2$ are independently $C_1$ to $C_{20}$ alkyl, $R^3$ is selected from H or an aliphatic rest, $R^4$ is selected from H or an aliphatic rest, AO represents at least one alkylene oxide, n is a number from 0 to 100.

Preferably, $R^1$ and $R^2$ are independently selected from $C_1$ to $C_4$ alkyl.

In one embodiment $R^1$ and $R^2$ are methyl.

In one embodiment $R^1$ and $R^2$ are ethyl.

Preferably $R^3$ is selected from $C_1$ to $C_4$ alkyl.

In one embodiment $R^3$ is methyl.

In one embodiment $R^3$ is ethyl.

Preferably $R^4$ is H or $C_1$-$C_{20}$ alkyl, more preferably H or $C_1$-$C_{12}$ alkyl, even more preferably H or $C_1$-$C_4$ alkyl.

In one embodiment $R_4$ is methyl.

In one embodiment $R_4$ is ethyl.

In one embodiment $R_4$ is propyl.

In one embodiment $R_4$ is butyl.

In one embodiment, alkylene oxides AO is one or more selected from a group consisting of ethylene oxide (EO), propylene oxide (PO), 1,2-butylene oxide or tetrahydrofurane.

When reference is made herein to solvents S comprising alkylene oxides AO, this shall mean said alkylene oxides are comprised in the molecule in ring opened form.

In one embodiment, alkylene oxide AO is one or more selected from a group consisting of —$CH_2$—$CH_2$—O—, —$CH_2$—$CH(CH_3)$—O—, —$CH_2$—$CH(CH_2$—$CH_3)$—O— or $(CH_2)_4$—O—.

In one embodiment solvents S comprise two or more types of alkylene oxides AO as block copolymers.

In one embodiment solvents S comprise two or more types of alkylene oxides AO as random polymers.

In one embodiment alkylene oxides AO in formula I are homopolymers of EO.

In one embodiment alkylene oxides AO in formula I are homopolymers of PO.

In one embodiment alkylene oxides AO in formula I are copolymers of EO and PO.

In one embodiment alkylene oxides AO in formula I are block copolymers of EO and PO.

In one embodiment alkylene oxides AO in formula I are block copolymers of the structure polyethylene oxide (PEO)-polypropylene oxide (PPO)-PEO.

In one embodiment alkylene oxides AO in formula I are random copolymers of EO and PO.

"n" is a number from 0 to 100, preferably 0 to 50, more preferably 0 to 10 and even more preferably 0 to 3.

In one embodiment "n" is a number from 1 to 100, preferably 1 to 50, more preferably 1 to 10 and even more preferably 1 to 3.

In one embodiment solvent S comprises more than 50% by weight of at least one compound according to formula (II)

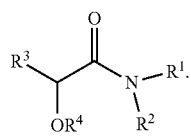

(II)

Preferably, $R^1$ and $R^2$ are independently selected from $C_1$ to $C_4$ alkyl.

In one embodiment $R^1$ and $R^2$ are methyl.
In one embodiment $R^1$ and $R^2$ are ethyl.
Preferably $R^3$ is selected from $C_1$ to $C_4$ alkyl.
In one embodiment $R^3$ is methyl.
In one embodiment $R^3$ is ethyl.
Preferably $R^4$ is H or $C_1$-$C_{20}$ alkyl, more preferably H or $C_1$-$C_{12}$ alkyl, even more preferably H or $C_1$-$C_4$ alkyl.
In one embodiment $R_4$ is methyl.
In one embodiment $R_4$ is ethyl.
In one embodiment $R_4$ is propyl.
In one embodiment $R_4$ is butyl.
In one embodiment, solvent S comprises more than 50% by weight of at least one compound according to formula (III).

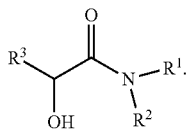

(III)

Preferably, $R^1$ and $R^2$ are independently selected from $C_1$ to $C_4$ alkyl.

In one embodiment $R^1$ and $R^2$ are methyl.
In one embodiment $R^1$ and $R^2$ are ethyl.
Preferably $R^3$ is selected from $C_1$ to $C_4$ alkyl.
In one embodiment $R^3$ is methyl.
In one embodiment $R^3$ is ethyl.

In preferred embodiments, said at least one solvent S comprises more than 50% by weight, preferably more than 70% by weight, more preferably more than 90% by weight and especially preferably more than 95% by weight of N,N-dimethyl-2-hydroxypropanoic amide and/or N,N-diethyl-2-hydroxypropanoic amide.

In further preferred embodiments, said at least one solvent S comprises more than 50% by weight, preferably more than 70% by weight, more preferably more than 90% by weight and especially preferably more than 95% by weight of N,N-dimethyl-2-methoxypropanoic amide and/or N,N-diethyl-2-methpropanoic amide.

Further solvents suitable for use in combination with solvents according to formula (I) include N-methylpyrrolidone, N,N-Dimethylacetamide and alcohols, preferably divalent alcohols or trivalent alcohols Suitable alcohols include n-butanol, sec.-butanol, isobutanol, n-pentanol, sec.-pentanol, iso-pentanol, 1,2-ethanediol, ethylene glycol, diethylene glycol, triethylene glycol, propyleneglycol, dipropyleneglycol, glycerol, neopentylglycol, 1,4-butanediol, 1,5-pentanediol.

In one embodiment, solvent S is N,N-dimethyl-2-hydroxypropanoic amide.
In one embodiment, solvent S is N,N-diethyl-2-hydroxypropanoic amide.

In one embodiment, solvent S is N,N-dimethyl-2-methoxypropanoic amide.
In one embodiment, solvent S is N,N-diethyl-2-methoxypropanoic amide.
In one embodiment, said at least one solvent S consists essentially of dimethyl-2-hydroxypropanoic amide.
In one embodiment, said at least one solvent S consists essentially of diethyl-2-hydroxypropanoic amide.

In addition to polymer P and solvent S, dope solution D can optionally further comprise further additives. For example dope solution may further comprise second dope polymers DP2. Suitable second dope polymers DP2 include polyvinylpyrrolidone, or polyalkylene oxides.

Suitable polyalkylene oxides are particularly polyethers of diols. Suitable polyalkylene oxides are normally produced by polymerization of at least one alkylene oxide. Suitable monomeric alkylene oxides are for example ethylene oxide or substituted ethylene oxides bearing one or more alkyl and/or aryl groups. Suitable monomeric alkylene oxides are for example styrene oxide or $C_2$-$C_{20}$-alkylene oxides, such as ethylene oxide, propylene oxide, 1,2-butylene oxide, 2,3-butylene oxide, isobutylene oxide, pentene oxide, hexene oxide, cyclohexene oxide, dodecene epoxide, octadecene epoxide. Ethylene oxide, propylene oxide, 1,2-butylene oxide, 2,3-butylene oxide, isobutylene oxide and pentene oxide are particularly suitable, propylene oxide and ethylene oxide being particularly preferred.

Suitable polyalkylene oxides can be homopolymers or copolymers.

In one embodiment, suitable polyalkylene oxides are copolymers of at least two different alkylene oxides. In one embodiment, suitable polyalkylene oxides are statistical copolymers of at least two different alkylene oxides. In another embodiment, suitable polyalkylene oxides are block copolymers of at least two different alkylene oxides.

In one preferred embodiment, suitable polyalkylene oxides are homopolymers of ethyleneoxide ("polyethylene oxide") or propylene oxide ("polypropylene oxide").

In one embodiment, suitable polyalkylene oxides are statistical copolymers of ethylene oxide and propylene oxide.

In one embodiment, suitable polyalkylene oxides are block copolymers of ethylene oxide and propylene oxide.

Suitable polyalkylene oxides can be linear or branched. Branching of a polyalkylene oxide can for example be achieved by including monomers bearing an epoxide group and an OH or a chloro moiety into the polyalkylene oxide. Preferably, suitable polyalkylene oxides are linear.

In one embodiment polyalkylene oxide blocks comprise 1 to 500 alkyleneoxide units. Preferably, suitable polyalkylene oxides comprise 2 to 300, more preferably 3 to 150, even more preferably 5 to 100 and especially preferably 10 to 80 alkylene oxide units.

In one embodiment second dope polymers DP2 are polyalkylene oxides with a molecular mass Mw of more than 100,000 g/mol or a K-value of more than 60 (Mw and K value determined as described in the experimental section).

In one embodiment, said at least one dope polymer DP2 is a polyalkylene oxide with a molar mass Mw of 100 kDa to 600 kDa.

In one embodiment, said at least one dope polymer DP2 has a molar mass Mw of 100 kDa to 400 kDa.

In one embodiment, said at least one dope polymer DP2 has a molar mass of Mw 300 kDa to 600 kDa.

In one embodiment, said at least one dope polymer DP2 is a polyalkylene oxide with a K-value of 60 to 200.

In one embodiment, said at least one dope polymer DP2 is a polyalkylene oxide with a K-value of 80 to 120.

In one embodiment, dope solution D comprises 5 to 30% by weight of polyarylene ether like polyethersulfone, 1 to 10% by weight of at least one second dope polymer DP2 like polyethylene oxide or polyvinylpyrrolidone and 60 to 94% by weight of at least one solvent S, with the proviso that the amounts add up to 100%.

The Dope solutions described above are storage stable and can be stored over longer periods of time, for example 1 week or 1 month, without showing any turbidity.

In step b) of processes according to the invention, at least coagulant C is added to said dope solution D. Thereby, said at least one polymer P is coagulated to obtain membrane M.

Coagulants C have lower solubility of polymer P than solvent S. Coagulants C are different from compounds according to formula (I).

Suitable coagulants C comprise for example liquid water, water vapor, alcohols or mixtures thereof. In one embodiment coagulants C are liquid water, water vapor, alcohols or mixtures thereof.

Preferably alcohols suitable as coagulants C are mono-, di- or trialkanols bearing no further functional groups like iso-propanol, ethylene glycol or propylene glycol.

Manufacturing of membranes M, especially of ultrafiltration membranes M, often includes non-solvent induced phase separation (NIPS).

In the NIPS process, the polymers used as starting materials (e.g. selected from polyvinyl pyrrolidone, vinyl acetates, cellulose acetates, polyacrylonitriles, polyamides, polyolefines, polyesters, polysulfones, polyethersulfones, polycarbonates, polyether ketones, sulfonated polyether ketones, polyamide sulfones, polyvinylidene fluorides, polyvinylchlorides, polystyrenes and polytetrafluorethylenes, copolymers thereof, and mixtures thereof; preferably selected from the group consisting of polysulfones, polyethersulfones, polyphenylene sulfones, polyvinylidene fluorides, polyamides, cellulose acetate and mixtures thereof, especially including polyether sulfone) are dissolved in at least one solvent S together with any additive(s) used. In a next step, a porous polymeric membrane is formed under controlled conditions in a coagulation bath. In most cases, the coagulation bath contains water as coagulant, or the coagulation bath is an aqueous medium, wherein the matrix forming polymer is not soluble. The cloud point of the polymer is defined in the ideal ternary phase diagram. In a bimodal phase separation, a microscopic porous architecture is then obtained, and water soluble components (including polymeric additives) are finally found in the aqueous phase.

In case further additives like second dope polymers DP2 are present that are simultaneously compatible with the coagulant C and the matrix polymer(s), segregation on the surface results. With the surface segregation, an enrichment of the certain additives is observed. The membrane surface thus offers new (hydrophilic) properties compared to the primarily matrix-forming polymer, the phase separation induced enrichment of the additive of the invention leading to antiadhesive surface structures.

A typical process for the preparation of a solution to prepare membranes is characterized by the following steps:
a) providing a dope solution D comprising at least one polymer P and at least one solvent S, wherein said at least one solvent S comprises more than 50% by weight of at least one compound according to formula (I)

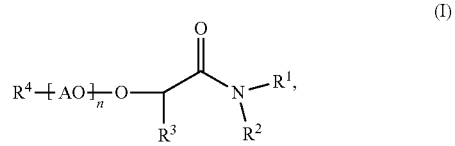

wherein $R^1$ and $R^2$ are independently $C_1$ to $C_{20}$ alkyl,
$R^3$ is selected from H or an aliphatic rest,
$R^4$ is selected from H or an aliphatic rest,
AO represents one or more alkylene oxides,
n is a number from 0 to 100.

a2) Adding further additives like pore forming additives such as PVP, PEG, sulfonated PESU or mixtures thereof, a3) Heating the mixture until a viscous solution is obtained; typically temperature of the dope solution D is 5-250° C., preferably 25-150° C., more preferably 50-90° C.

a4) Stirring of the solution/suspension until a mixture is formed within 1-15 h, typically the homogenization is finalized within 2 h.

b) Casting the membrane dope in a coagulation bath to obtain a membrane structure. Optionally the casting can be outlined using a polymeric support (non-woven) for stabilizing the membrane structure mechanically.

In one embodiment, hollow fiber membranes or multibore membranes (multichannel hollow fiber membranes) are manufactured by extruding a polymer, which forms a semipermeable membrane after coagulation through an extrusion nozzle with several hollow needles. A coagulating liquid is injected through the hollow needles into the extruded polymer during extrusion, so that parallel continuous channels extending in extrusion direction are formed in the extruded polymer. Preferably the pore size on an outer surface of the extruded membrane is controlled by bringing the outer surface after leaving the extrusion nozzle in contact with a mild coagulation agent such that the shape is fixed without active layer on the outer surface and subsequently the membrane is brought into contact with a strong coagulation agent. As a result a membrane can be obtained that has an active layer inside the channels and an outer surface, which exhibits no or hardly any resistance against liquid flow. Herein suitable coagulation agents include solvents and/or non-solvents. The strength of the 0 may be adjusted by the combination and ratio of non-solvent/solvent. Coagulation solvents are known to the person skilled in the art and can be adjusted by routine experiments.

Optionally processes according to the invention can be followed by further process steps. For example such processes may include c) oxidative treatment of the membrane previously obtained, for example using sodium hypochlorite. Such processes are for example described in I. M. Wienk, E. E. B. Meuleman, Z. Borneman, Th. Van den Boomgaard, C. A. Smoulders, Chemical Treatment of Membranes of a Polymer Blend: Mechanism of the reaction of hypochlorite with poly(vinylpyrrolidone), *Journal of Polymer Science: Part A: Polymer Chemistry* 1995, 33, 49-54.

Processes according to the invention may further comprise d) washing of the membrane with water.

Processes according to the invention are easy and economical to carry out and allow for the manufacture of membranes M with excellent separation characteristics, mechanical stability and fouling properties.

Membranes M have excellent separation characteristics. In particular, membranes M have very good molecular weight cutoffs (MWCO). In a preferred embodiment, membranes M have a molecular weight cutoff, determined as described in the experimental section, of less than 20 kDa.

Membranes M further have very good water permeabilities. In a preferred embodiment, membranes M have a pure water permeability (PWP), determined as described in the experimental section, of at least 200 kg/h m² bar, in many cases in the range from 230 to 740 kg/h m² bar, preferably of more than 500 kg/h m² bar.

Membranes M have very good fouling properties and show only little fouling and biofouling.

Membranes M are storage stable and have a long lifetime.

Another aspect of the invention are membranes obtained using processes according to the invention as described above.

Another aspect of the invention is the use of membranes M.

In a preferred embodiment, membranes M are used for the treatment of sea water or brackish water or surface water.

In one preferred embodiment of the invention, membranes according to the invention, particularly RO, FO or NF membranes are used for the desalination of sea water or brackish water.

Membranes M, particularly RO, FO or NF membranes are used for the desalination of water with a particularly high salt content of for example 3 to 8% by weight. For example membranes M are suitable for the desalination of water from mining and oil/gas production and fracking processes, to obtain a higher yield in these applications.

Different types of membrane M can also be used together in hybrid systems combining for example RO and FO membranes, RO and UF membranes, RO and NF membranes, RO and NF and UF membranes, NF and UF membranes.

In another preferred embodiment, membranes M, particularly NF, UF or MF membranes are used in a water treatment step prior to the desalination of sea water or brackish water.

In another preferred embodiment membranes M, particularly NF, UF or MF membranes are used for the treatment of industrial or municipal waste water.

Membranes M, particularly RO and/or FO membranes can be used in food processing, for example for concentrating, desalting or dewatering food liquids (such as fruit juices), for the production of whey protein powders and for the concentration of milk, the UF permeate from making of whey powder, which contains lactose, can be concentrated by RO, wine processing, providing water for car washing, making maple syrup, during electrochemical production of hydrogen to prevent formation of minerals on electrode surface, for supplying water to reef aquaria.

Membranes M, particularly UF membranes can be used in medical applications like in dialysis and other blood treatments, food processing, concentration for making cheese, processing of proteins, desalting and solvent-exchange of proteins, fractionation of proteins, clarification of fruit juice, recovery of vaccines and antibiotics from fermentation broth, laboratory grade water purification, drinking water disinfection (including removal of viruses), removal of endocrines and pesticides combined with suspended activated carbon pretreatment.

Membranes M, particularly RO, FO, NF membranes can be used for rehabilitation of mines, homogeneous catalyst recovery, desalting reaction processes.

Membranes M, particularly NF membranes, can be used for separating divalent ions or heavy and/or radioactive metal ions, for example in mining applications, homogeneous catalyst recovery, desalting reaction processes.

EXAMPLES

Abbreviations used in the examples and elsewhere:
NMP N-methylpyrrolidone
DMAc Dimethylacetamide
PWP pure water permeation
MWCO molecular weight cutoff
DMF dimethylformamide
THF tetrahydrofurane
PESU polyethersulfone
AMD3L N,N-Dimethyl-lactamide
Ultrason® E 6020P polyethersulfone with a viscosity number (ISO 307, 1157, 1628; in 0.01 g/mol phenol/1,2 orthodichlorobenzene 1:1 solution) of 82; a glass transition temperature (DSC, 10° C./min; according to ISO 11357-1/-2) of 225° C.; a molecular weight Mw (GPC in DMAc, PMMA standard): 75000 g/mol
Luvitec® K90 Polyvinylpyrrolidone with a solution viscosity characterized by the K-value of 90, determined according to the method of Fikentscher (Fikentscher, Cellulosechemie 13, 1932 (58))
Luvitec® K30 Polyvinylpyrrolidone with a solution viscosity characterized by the K-value of 30, determined according to the method of Fikentscher (Fikentscher, Cellulosechemie 13, 1932 (58))
POLYOX™ WSR-N10 Polyethyleneoxide with a solution viscosity characterized by the K-value of 68, determined according to the method of Fikentscher (Fikentscher, Cellulosechemie 13, 1932 (58)) and a molecular weight Mw (GPC in water, polyethyleneoxide standard): 102000 g/mol
POLYOX™ WSR-N80 Polyethyleneoxide with a solution viscosity characterized by the K-value of 84, determined according to the method of Fikentscher (Fikentscher, Cellulosechemie 13, 1932 (58)) and a molecular weight Mw (GPC in water, polyethyleneoxide standard): 187000 g/mol
POLYOX™ WSR-N750 Polyethyleneoxide with a solution viscosity characterized by the K-value of 109, determined according to the method of Fikentscher (Fikentscher, Cellulosechemie 13, 1932 (58)) and a molecular weight Mw (GPC in water, polyethyleneoxide standard): 456000 g/mol
Pluriol® 9000E Polyethyleneoxide with a solution viscosity characterized by the K-value of 33, determined according to the method of Fikentscher (Fikentscher, Cellulosechemie 13, 1932 (58)) and a molecular weight Mw (GPC in water, polyethyleneoxide standard): 10800 g/mol
Breox® 75W55000 Polyethyleneoxide-polypropyleneoxide copolymer with a solution viscosity characterized by the K-value of 42, determined according to the method of Fikentscher (Fikentscher, Cellulosechemie 13, 1932 (58)) and a molecular weight Mw (GPC in water, polyethyleneoxide standard): 14300 g/mol The molecular weight distribution and the average molecular weight of the polyalkyleneoxide polymers obtained were determined by GPC measurements. GPC-measurements were done using water as solvent. After filtration (pore size 0.2 μm), 100 μl of this solution was injected in the GPC system. For the separation two hydroxylated polymethacrylate columns (TSKgel GMPWXL, 30 cm) were used. The system was operated with a flow rate of 0.8 ml/min at 35° C. As detection system an RI-detector was used (DRI Agilent 1100). The calibration was carried out with polyethyleneoxide-standards (company Polymer Labs, Agilent easy vial) with molecular weights in the range from 106 to 1,522,000 g/mol.

The pure water permeation (PWP) of the membranes was tested using a pressure cell with a diameter of 60 mm using ultrapure water (salt-free water, filtered by a Millipore U F-system).

In a subsequent test, a solution of different PEG-Standards was filtered at a pressure of 0.15 bar. By GPC-measurements of the feed and permeate, the molecular weight cut-off of the membranes was determined.

Examples 1 to 5: Preparation of Membranes Using Polyvinylpyrrolidone as Second Dope Polymer Into a three neck flask equipped with a magnetic stirrer there were added 75 ml of Solvent S1 as given in table 1, Luvitec K30 ("K30") and Luvitec K90 ("K90") as second dope polymers with the amounts given in table 1 and 19 g of polyethersulfone (Ultrason® E 6020P). The mixture was heated under gentle stirring at 60° C. until a homogeneous clear viscous solution was obtained. The solution was degassed overnight at room temperature. After that the membrane solution was reheated at 60° C. for 2 hours and casted onto a glass plate with a casting knife (300 microns) at 60° C. using an Erichsen Coating machine operating at a speed of 5 mm/min. The membrane film was allowed to rest for 30 seconds before immersion in a water bath at 25° C. for 10 minutes. After the membrane had detached from the glass plate, the membrane was carefully transferred into a water bath for 12 h. Afterwards the membrane was transferred into a bath containing 2500 ppm NaOCl at 50° C. for 4.5 h. The membrane was then washed with water at 60° C. and one time with a 0.5 wt.-% solution of sodium bisulfite to remove active chlorine. After several washing steps with water the membrane was stored wet until characterization regarding pure water permeability (PWP) and minimum pore size (MWCO) started.

TABLE 1

Compositions and properties of membranes prepared according to examples 1 to 5; MWCO in [Da], PWP in [kg/h m²bar].

|   | K30 | K90 | Solvent S1 | PWP | MWCO |
|---|-----|-----|------------|-----|------|
| 1 | 0 | 6 | AMD3L | 230 | 6800 |
| 2 | 3 | 3 | AMD3L | 360 | 12100 |
| 3 | 2 | 4 | AMD3L | 740 | 17000 |
| 4 | 1 | 5 | AMD3L | 360 | 13200 |
| 5 | 0 | 6 | NMP | 510 | 42400 |

Examples 6 to 13: Preparation of Membranes Using Polyalkyleneoxides as Second Dope Polymer Into a three neck flask equipped with a magnetic stirrer there were added 75 ml of Solvent S1 as given in table 1, POLYOX™ WSR-N10 ("N10"), POLYOX™ WSR-N80 ("N80"), POLYOX™ WSR-N750 ("N750"), Breox® 75W55000 ("Breox") and/or Pluriol® 9000E ("P9000") as second dope polymers with the amounts given in table 2 and 19 g of polyethersulfone (Ultrason® E 6020P). The mixture was heated under gentle stirring at 60° C. until a homogeneous clear viscous solution was obtained. The solution was degassed overnight at room temperature. After that the membrane solution was reheated at 60° C. for 2 hours and casted onto a glass plate with a casting knife (300 microns) at 60° C. using an Erichsen Coating machine operating at a speed of 5 mm/min. The membrane film was allowed to rest for 30 seconds before immersion in a water bath at 25° C. for 10 minutes.

After the membrane had detached from the glass plate, the membrane was carefully transferred into a water bath for 12 h. Then, the membrane was transferred into a bath containing 2500 ppm NaOCl at 50° C. for 4.5 h to remove polyalkyleneoxides. The membrane was then washed with water at 60° C. and one time with a 0.5 wt.-% solution of sodium bisulfite to remove active chlorine. After several washing steps with water the membrane was stored wet until characterization regarding pure water permeability (PWP) and minimum pore size (MWCO) started.

TABLE 2

Compositions and properties of membranes prepared according to examples 6 to 13; MWCO in [Da], PWP in [kg/h m²bar].

|    | N10 | N80 | N750 | P9000 | Breox | Solvent S1 | PWP | MWCO |
|----|-----|-----|------|-------|-------|------------|-----|------|
| 6  | 6   |     |      |       |       | AMD3L | 530 | 9500 |
| 7  | 6   |     |      |       |       | NMP   | 420 | 12000 |
| 8  |     | 6   |      |       |       | AMD3L | 460 | 9100 |
| 9  |     | 6   |      |       |       | NMP   | 380 | 8900 |
| 10 |     |     | 3    | 3     |       | AMD3L | 530 | 16250 |
| 11 |     |     | 3    | 3     |       | NMP   | 550 | 29200 |
| 12 |     |     | 3    |       | 3     | AMD3L | 710 | 9200 |
| 13 |     |     | 3    |       | 3     | NMP   | 700 | 14600 |

Membranes produced with AMD3L according to the invention show improved separation characteristics over membranes known from the art. Membranes produced with AMD3L show improved (smaller) MWCO while maintaining the permeabilities of membranes known from the art.

The invention claimed is:

1. A process for making membranes M, comprising:
    a) providing a dope solution D comprising at least one polymer P and a solvent S, wherein the at least one polymer P is selected from the group consisting of poly(vinylidene fluoride) (PVDF), polysulfone (PSU), polyphenylenesulfone (PPSU), polyethersulfone (PESU), and mixtures thereof; and
    b) adding at least one coagulant C to the dope solution D to coagulate the at least one polymer P from the dope solution D to obtain membrane M,
    wherein the solvent S is N,N-dimethyl-2-hydroxypropanoic amide or N,N-diethyl-2-hydroxypropanoic amide.

2. The process according to claim 1, wherein the at least one coagulant C comprises water or water vapor.

3. The process according to claim 1, wherein the dope solution D further comprises 0.1 to 10% by weight, based on a weight of the of the dope solution, of additives selected from polyvinylpyrrolidone, and polyalkylene oxides.

4. The process according to claim 1, wherein after a) and b) the membrane M is subjected to an oxidative treatment.

5. The process according to claim 1, wherein the membrane M is an ultrafiltration membrane, a microfiltration membrane or a component of a reverse osmosis or forward osmosis membrane.

6. A membrane obtained according to the process according to claim 1.

7. A membrane element comprising membranes obtained in the process according to claim 1.

8. A membrane module comprising membranes obtained in the process according to claim 1.

9. A filtration system comprising the membrane modules according to claim 8.

10. A filtration system comprising the membrane elements according to claim 7.

11. The process according to claim 1, further comprising after a) and b), washing the membrane with water.

* * * * *